United States Patent
Simpson et al.

(10) Patent No.: US 7,074,307 B2
(45) Date of Patent: Jul. 11, 2006

(54) ELECTRODE SYSTEMS FOR ELECTROCHEMICAL SENSORS

(75) Inventors: Peter C. Simpson, Del Mar, CA (US); James R. Petisce, San Diego, CA (US); Victoria Carr-Brendel, Pleasanton, CA (US); James H. Brauker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 108 days.

(21) Appl. No.: 10/897,312

(22) Filed: Jul. 21, 2004

(65) Prior Publication Data

US 2005/0115832 A1 Jun. 2, 2005

Related U.S. Application Data

(60) Provisional application No. 60/490,007, filed on Jul. 25, 2003.

(51) Int. Cl.
*G01N 27/327* (2006.01)
*A61B 5/05* (2006.01)

(52) U.S. Cl. .............. 204/403.04; 204/403.1; 204/403.11; 600/345; 600/347

(58) Field of Classification Search .............. 204/403.01–403.15, 416–418; 205/777.5, 205/778; 600/345, 347
See application file for complete search history.

(56) References Cited

U.S. PATENT DOCUMENTS

| | | | |
|---|---|---|---|
| 4,255,500 A | 3/1981 | Hooke | |
| 4,374,013 A | 2/1983 | Enfors | |
| 4,388,166 A | 6/1983 | Suzuki et al. | |
| 4,431,004 A | 2/1984 | Bessman et al. | |
| 4,431,507 A * | 2/1984 | Nankai et al. | 204/403.11 |
| 4,671,288 A | 6/1987 | Gough | |
| 4,703,756 A | 11/1987 | Gough et al. | |
| 4,721,677 A | 1/1988 | Clark, Jr. | |
| 4,757,022 A | 7/1988 | Shults et al. | |
| 4,776,944 A | 10/1988 | Janata et al. | |
| 4,781,798 A | 11/1988 | Gough | |
| 4,890,620 A | 1/1990 | Gough | |
| 4,994,167 A | 2/1991 | Shults et al. | |

(Continued)

FOREIGN PATENT DOCUMENTS

EP  0539625 A1 *  5/1993

(Continued)

OTHER PUBLICATIONS

U.S. Appl. No. 10/897,377 filed Jul. 21, 2004.*

(Continued)

*Primary Examiner*—Alex Noguerola
(74) *Attorney, Agent, or Firm*—Knobbe, Martens, Olson & Bear, LLP

(57) ABSTRACT

The present invention relates generally to systems and methods for improved electrochemical measurement of analytes. The preferred embodiments employ electrode systems including an analyte-measuring electrode for measuring the analyte or the product of an enzyme reaction with the analyte and an auxiliary electrode configured to generate oxygen and/or reduce electrochemical interferants. Oxygen generation by the auxiliary electrode advantageously improves oxygen availability to the enzyme and/or counter electrode; thereby enabling the electrochemical sensors of the preferred embodiments to function even during ischemic conditions. Interferant modification by the auxiliary electrode advantageously renders them substantially non-reactive at the analyte-measuring electrode, thereby reducing or eliminating inaccuracies in the analyte signal due to electrochemical interferants.

50 Claims, 4 Drawing Sheets

U.S. PATENT DOCUMENTS

| | | | |
|---|---|---|---|
| 5,030,333 | A | 7/1991 | Clark, Jr. |
| 5,140,985 | A | 8/1992 | Schroeder et al. |
| 5,198,771 | A | 3/1993 | Fidler et al. |
| 5,411,647 | A | 5/1995 | Johnson et al. |
| 5,428,123 | A | 6/1995 | Ward et al. |
| 5,431,160 | A | 7/1995 | Wilkins |
| 5,496,453 | A | 3/1996 | Uenoyama et al. |
| 5,571,395 | A | 11/1996 | Park et al. |
| 5,605,152 | A | 2/1997 | Slate et al. |
| 5,628,890 | A | 5/1997 | Carter et al. |
| 5,653,863 | A | 8/1997 | Genshaw et al. |
| 5,686,829 | A | 11/1997 | Girault |
| 5,795,774 | A | 8/1998 | Matsumoto et al. |
| 5,914,026 | A | 6/1999 | Blubaugh, Jr. et al. |
| 5,964,993 | A | 10/1999 | Blubaugh et al. |
| 5,965,380 | A | 10/1999 | Heller et al. |
| 5,985,129 | A | 11/1999 | Gough et al. |
| 5,999,848 | A | 12/1999 | Gord et al. |
| 6,001,067 | A | 12/1999 | Shults et al. |
| 6,066,448 | A * | 5/2000 | Wohlstadter et al. .......... 435/6 |
| 6,081,735 | A | 6/2000 | Diab et al. |
| 6,081,736 | A | 6/2000 | Colvin et al. |
| 6,088,608 | A | 7/2000 | Schulman et al. |
| 6,119,028 | A | 9/2000 | Schulman et al. |
| 6,120,676 | A | 9/2000 | Heller et al. |
| 6,122,536 | A | 9/2000 | Sun et al. |
| 6,134,461 | A | 10/2000 | Say et al. |
| 6,141,573 | A | 10/2000 | Kurnik et al. |
| 6,144,869 | A | 11/2000 | Berner et al. |
| 6,189,536 | B1 | 2/2001 | Martinez et al. |
| 6,212,416 | B1 | 4/2001 | Ward et al. |
| 6,264,825 | B1 * | 7/2001 | Blackburn et al. ....... 205/777.5 |
| 6,274,285 | B1 | 8/2001 | Gries et al. |
| 6,300,002 | B1 | 10/2001 | Webb et al. |
| 6,325,979 | B1 | 12/2001 | Hahn et al. |
| 6,329,161 | B1 | 12/2001 | Heller et al. |
| 6,356,776 | B1 | 3/2002 | Berner et al. |
| 6,400,974 | B1 | 6/2002 | Lesho |
| 6,466,810 | B1 | 10/2002 | Ward et al. |
| 6,512,939 | B1 | 1/2003 | Colvin et al. |
| 6,514,718 | B1 | 2/2003 | Heller et al. |
| 6,542,765 | B1 | 4/2003 | Guy et al. |
| 6,546,268 | B1 | 4/2003 | Ishikawa et al. |
| 6,551,496 | B1 | 4/2003 | Moles et al. |
| 6,558,321 | B1 | 5/2003 | Burd et al. |
| 6,595,919 | B1 | 7/2003 | Berner et al. |
| 6,615,078 | B1 | 9/2003 | Burson et al. |
| 6,618,934 | B1 | 9/2003 | Feldman et al. |
| 6,702,857 | B1 | 3/2004 | Brauker et al. |
| 6,741,877 | B1 | 5/2004 | Shults et al. |
| 6,809,507 | B1 | 10/2004 | Morgan et al. |
| 6,862,465 | B1 | 3/2005 | Shults et al. |
| 6,891,317 | B1 | 5/2005 | Pei et al. |
| 6,892,085 | B1 | 5/2005 | McIvor et al. |
| 2003/0032874 | A1 | 2/2003 | Rhodes et al. |
| 2003/0050546 | A1 | 3/2003 | Desai et al. |
| 2004/0106857 | A1 | 6/2004 | Gough |
| 2004/0219664 | A1 | 11/2004 | Heller et al. |
| 2005/0027180 | A1 | 2/2005 | Goode et al. |
| 2005/0027181 | A1 | 2/2005 | Goode et al. |
| 2005/0027463 | A1 | 2/2005 | Goode et al. |
| 2005/0031689 | A1 | 2/2005 | Shults et al. |
| 2005/0033132 | A1 | 2/2005 | Shults et al. |
| 2005/0043598 | A1 | 2/2005 | Goode et al. |
| 2005/0051427 | A1 | 3/2005 | Brauker et al. |
| 2005/0051440 | A1 | 3/2005 | Simpson et al. |
| 2005/0054909 | A1 | 3/2005 | Petisce et al. |
| 2005/0056552 | A1 | 3/2005 | Simpson et al. |
| 2005/0090607 | A1 | 4/2005 | Tapsak et al. |
| 2005/0112169 | A1 | 5/2005 | Brauker et al. |
| 2005/0192557 | A1 | 9/2005 | Brauker et al. |

FOREIGN PATENT DOCUMENTS

| | | |
|---|---|---|
| EP | 1153571 A1 | 11/2001 |
| FR | 2 656 423 | 6/1991 |
| GB | 1 442 303 | 7/1976 |
| JP | 62083849 | 4/1987 |
| WO | WO 94/22367 | 10/1994 |
| WO | WO 99/58051 | 11/1999 |
| WO | WO 01/68901 A2 | 9/2001 |
| WO | WO 01/88524 A1 | 11/2001 |
| WO | WO 04/021877 A1 | 3/2004 |

OTHER PUBLICATIONS

Bott, A.W. 1997. A comparison of cyclic voltammetry and staircase voltammetry. Current Separations, 16(1):23-26.*

Wilson, et al. 1992. Progress toward the development of an implantable sensor for glucose. Clin. Chem., 38(9):1613-1617.*

Abel, P. U.; von Woedtke, T. Biosensors for in vivo glucose measurement: can we cross the experimental stage. Biosens Bioelectron 2002, 17, 1059-1070.

Baker, et al. 1993. Dynamic concentration challenges for biosensor characterization. *Biosensors & Bioelectronics*,8:433-441.

Bindra, et al. 1989. Pulsed amperometric detection of glucose in biological fluids at a surface-modified gold electrode. *Anal Chem*, 61:2566-2570.

Bisenberger, et al. 1995. A triple-step potential waveform at enzyme multisensors with thick-film gold electrodes for detection of glucose and sucrose. *Sensors and Actuators*, B 28:181-189.

Bott, A. 1998. Electrochemical methods for the determination of glucose. *Current Separations*, 17(1):25-31.

Choleau, et al. 2002. Calibration of a subcutaneo amperometric glucose sensor. Part 1. Effect of measurement uncertainties on the determination of sensor sensitivity and background current. *Biosensors and Bioelectronics*, 17:641-646.

Dixon, et al. 2002. Characterization in vitro and in vivo of the oxygen dependence of an enzyme/polymer biosensor for monitoring brain glucose. *Journal of Neuroscience Methods*, 119:135-142.

Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.

Hall, et al. 1998. Electrochemical oxidation of hydrogen peroxide at platinum electrodes. Part 1. An adsorption-controlled mechanism. *Electrochimica Acta*, 43(5-6):579-588.

Hall, et al. 1998. Electrochemical oxidation of hydrogen peroxide at platinum electrodes. Part II: Effect of potential. *Electrochimica Acta*, 43(14-15):2015-2024.

Hall, et al. 1999. Electrochemical oxidation of hydrogen peroxide at platinum electrodes. Part III: Effect of temperature. *Electrochimica Acta*, 44:2455-2462.

Hall, et al. 1999. Electrochemical oxidation of hydrogen peroxide at platinum electrodes. Part IV: Phosphate buffer dependence. *Electrochimica Acta*, 44:4573-4582.

Hall, et al. 2000. Electrochemical oxidation of hydrogen peroxide at platinum electrodes. Part V: Inhibition by chloride. *Electrochimica Acta*, 45:3573-3579.

Heller, A. Implanted electrochemical glucose sensors for the management of diabetes. Annu Rev Biomed Eng 1999, 1, 153-175.

Hitchman, M. L. 1978. "Measurement of Dissolved Oxygen." In Elving, et al. (Eds.). Chemical Analysis, vol. 49, Chap. 3, pp. 34-49, 59-123. New York: John Wiley & Sons.

Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Jablecki, et al. 2000. Simulations of the frequency response of implantable glucose sensors. *Analytical Chemistry*, 72:1853-1859.

Jaremko, et al. 1998. Advances toward the implantable artificial pancreas for treatment of diabetes. *Diabetes Care*, 21(3):444-450.

Jensen, et al. 1997. Fast wave forms for pulsed electrochemical detection of glucose by incorporation of reductive desorption of oxidation products. *Analytical Chemistry*, 69(9):1776-1781.

Kang, S. K.; Jeong, R.A.; Park, S.; Chung, T. D.; Park, S.; Kim, H. C. In vitro and short-term in vivo characteristics of a Kel-F thin film modified glucose sensor. Anal Sci 2003, 19, 1481-1486.

Kraver, K.; Gutha, M. R.; Strong, T.; Bird, P.; Cha, G.; Hoeld, W.; Brown, R. A mixed-signal sensor interface microinstrument. Sensors and Actuators A: Physical 2001, 91, 266-277.

LaCourse, et al. 1993. Optimization of waveforms for pulsed amperometric detection of carbohydrates based on pulsed voltammetry. *Analytical Chemistry*, 65:50-52.

Lemer, et al. 1984. An implantable electrochemical glucose sensor. *Ann. N. Y. Acad. Sci.*, 428:263-278.

Leypoldt, et al. 1984. Model of a two-substrate enzyme electrode for glucose. *Anal. Chem.*, 56:2896-2904.

McGrath, M. J.; Iwuoha, E. I.; Diamond, D.; Smyth, M. R. The use of differential measurements with a glucose biosensor for interference compensation during glucose determinations by flow injection analysis. Biosens Bioelectron 1995. 10, 937-943.

Memoli, A.; Annesini, M. C.; Mascini, M.; Papale, S.; Petralito, S. A comparison between different immobilised glucoseoxidase-based electrodes. J Pharm Biomed Anal 2002, 29, 1045-1052.

Neuburger, et al. 1987. Pulsed amperometric detection of carbohydrates at gold electrodes with a two-step potential waveform. *Anal. Chem.*, 59:150-154.

Postlethwaite, et al. 1996. Interdigitated array electrode as an alternative to the rotated ring-disk electrode for determination of the reaction products of dioxygen reduction. *Analytical Chemistry*, 68:2951-2958.

Rhodes, et al. 1994. Prediction of pocket-portable and implantable glucose enzyme electrode performance from combined species permeability and digital simulation analysis. *Analytical Chemistry*, 66(9):1520-1529.

Sansen, et al. 1990. A smart sensor for the voltammetric measurement of oxygen or glucose concentrations. *Sensors and Actuators*, B 1:298-302.

Wang, X.; Pardue, H. L. Improved ruggedness for membrane-based amperometric sensors using a pulsed amperometric method. Anal Chem 1997, 69, 4482-4489.

Ward, W. K.; Wood, M. D.; Troupe, J. E. Understanding Spontaneous Output Fluctuations of an Amperometric Glucose Sensor: Effect of Inhalation Anesthesia and e of a Nonenzyme Containing Electrode. ASAIO Journal 2000, 540-546.

Ward, et al. 2000. Rise in background current over time in a subcutaneous glucose sensor in the rabbit: Relevance to calibration and accuracy. *Biosensors & Bioelectronics*, 15:53-61.

Ward et al. 2002. A new amperometric glucose microsensor: In vitro and short-term in vivo evaluation. *Biosensors & Bioelectronics*, 17:181-189.

Wilkins, et al. 1995. Integrated implantable device for long-term glucose monitoring. *Biosens. Bioelectron.*, 10:485-494.

Wientjes, K. J. C. Development of a glucose sensor for diabetic patients. 2000.

Wilkins, E.; Atanasov, P. Glucose monitoring: state of the art and future possibilities. Med Eng Phys 1995, 18, 273-288.

Wu, et al. 1999. *In situ* electrochemical oxygen generation with an immunoisolation device. *Ann. N.Y. Acad. Sci.*, 875:105-125.

Zhang, et al. 1994. Elimination of the acetaminophen interference in an implantable glucose sensor. *Analytical Chemistry*, 66(7):1183-1188.

U.S. Appl. No. 09/447,227, filed Nov. 22, 1999.
U.S. Appl. No. 10/838,658 filed May 3, 2004.
U.S. Appl. No. 10/838,909 filed May 3, 2004.
U.S. Appl. No. 10/838,912 filed May 3, 2004.
U.S. Appl. No. 10/885,476 filed Jul. 6, 2004.

* cited by examiner

ELECTRODE SYSTEMS FOR ELECTROCHEMICAL SENSORS

RELATED APPLICATION

This application claims the benefit of priority under 35 U.S.C. § 119(e) to U.S. Provisional Application No. 60/490,007, filed Jul. 25, 2003, the contents of which are hereby incorporated by reference in their entirety.

FIELD OF THE INVENTION

The present invention relates generally to systems and methods for improving electrochemical sensor performance.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are spread apart so far that the diabetic will likely find out too late, sometimes incurring dangerous side effects, of a hyperglycemic or hypoglycemic condition. It is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate working of blood glucose. Similarly, transdermal sensors have problems in accurately working and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have occurred.

SUMMARY OF THE PREFERRED EMBODIMENTS

In contrast to the prior art, the sensors of preferred embodiments advantageously generate oxygen to allow the sensor to function at sufficient oxygen levels independent of the oxygen concentration in the surrounding environment. In another aspect of the preferred embodiments, systems and methods for modifying electrochemical interferants are provided.

Accordingly, in a first embodiment, an electrochemical sensor for determining a presence or a concentration of an analyte in a fluid is provided, the sensor comprising a membrane system comprising an enzyme, wherein the enzyme reacts with the analyte; an electroactive surface comprising a working electrode, the working electrode comprising a conductive material and configured to measure a product of the reaction of the enzyme with the analyte; and an auxiliary electrode comprising a conductive material and configured to generate oxygen, wherein the auxiliary electrode is situated such that the oxygen generated diffuses to the enzyme or to the electroactive surface.

In an aspect of the first embodiment, the auxiliary electrode comprises a conductive material selected from the group consisting of a conductive metal, a conductive polymer, and a blend of a conductive metal and a conductive polymer.

In an aspect of the first embodiment, the auxiliary electrode comprises a form selected from the group consisting of a mesh, a grid, and a plurality of spaced wires.

In an aspect of the first embodiment, the auxiliary electrode comprises a polymer, wherein the polymer is situated on a surface of the auxiliary electrode.

In an aspect of the first embodiment, the polymer comprises a material that is impermeable to glucose but is permeable to oxygen.

In an aspect of the first embodiment, the polymer comprises a material that is impermeable to glucose but is permeable to oxygen and permeable to interfering species.

In an aspect of the first embodiment, the polymer comprises a material having a molecular weight that blocks glucose and allows transport therethrough of oxygen, urate, ascorbate, and acetaminophen.

In an aspect of the first embodiment, the polymer comprises a material that is permeable to glucose and oxygen.

In an aspect of the first embodiment, the polymer comprises a material that is permeable to glucose, oxygen, and interfering species.

In an aspect of the first embodiment, the polymer comprises a material having a molecular weight that allows transport therethrough of oxygen, glucose, urate, ascorbate, and acetaminophen.

In an aspect of the first embodiment, the auxiliary electrode is configured to be set at a potential of at least about +0.6 V.

In an aspect of the first embodiment, the auxiliary electrode is configured to electrochemically modify an electrochemical interferant to render the electrochemical interferent substantially electrochemically non-reactive at the working electrode.

In an aspect of the first embodiment, the auxiliary electrode is configured to be set at a potential of at least about +0.1 V.

In a second embodiment, an electrochemical sensor for determining a presence or a concentration of an analyte in a fluid is provided, the sensor comprising a membrane system comprising an enzyme, wherein the enzyme reacts with the analyte; an electroactive surface comprising a working electrode, the working electrode comprising a conductive material and configured to measure a product of the reaction of the enzyme with the analyte; and an auxiliary electrode comprising a conductive material and configured to modify an electrochemical interferant such that the electrochemical interferent is rendered substantially electrochemically non-reactive at the working electrode.

In an aspect of the second embodiment, the auxiliary electrode comprises a conductive material selected from the group consisting of a conductive metal, a conductive polymer, and a blend of a conductive metal and a conductive polymer.

In an aspect of the second embodiment, the auxiliary electrode comprises a form selected from the group consisting of a mesh, a grid, and a plurality of spaced wires.

In an aspect of the second embodiment, the auxiliary electrode comprises a polymer, wherein the polymer is situated on a surface of the auxiliary electrode.

In an aspect of the second embodiment, the polymer comprises a material that is permeable to an electrochemical interferant.

In an aspect of the second embodiment, the polymer comprises a material that is impermeable to glucose but is permeable to oxygen.

In an aspect of the second embodiment, the polymer comprises a material that is impermeable to glucose but is permeable to oxygen and interferants.

In an aspect of the second embodiment, the polymer comprises a material having a molecular weight that blocks glucose and allows transport therethrough of oxygen, urate, ascorbate, and acetaminophen.

In an aspect of the second embodiment, the polymer comprises a material that is permeable to glucose and oxygen.

In an aspect of the second embodiment, the polymer comprises a material that is permeable to glucose, oxygen, and interferants.

In an aspect of the second embodiment, the polymer comprises a material having a molecular weight that allows transport therethrough of oxygen, glucose, urate, ascorbate, and acetaminophen.

In an aspect of the second embodiment, the auxiliary electrode is configured to be set at a potential of at least about +0.1V.

In an aspect of the second embodiment, the auxiliary electrode is configured to generate oxygen.

In an aspect of the second embodiment, the auxiliary electrode is configured to be set at a potential of at least about +0.6 V.

In a third embodiment, an electrochemical sensor is provided comprising an electroactive surface configured to measure an analyte; and an auxiliary interferant-modifying electrode configured to modify an electrochemical interferant such that the electrochemical interferant is rendered substantially non-reactive at the electroactive surface.

In an aspect of the third embodiment, the auxiliary interferant-modifying electrode comprises a conductive material selected from the group consisting of a conductive metal, a conductive polymer, and a blend of a conductive metal and a conductive polymer.

In an aspect of the third embodiment, the auxiliary interferant-modifying electrode comprises a form selected from the group consisting of a mesh, a grid, and a plurality of spaced wires.

In an aspect of the third embodiment, the auxiliary interferant-modifying electrode comprises a polymer, wherein the polymer is situated on a surface of the auxiliary interferant-modifying electrode.

DETAILED DESCRIPTION OF THE PREFERRED EMBODIMENT

Figure 1:
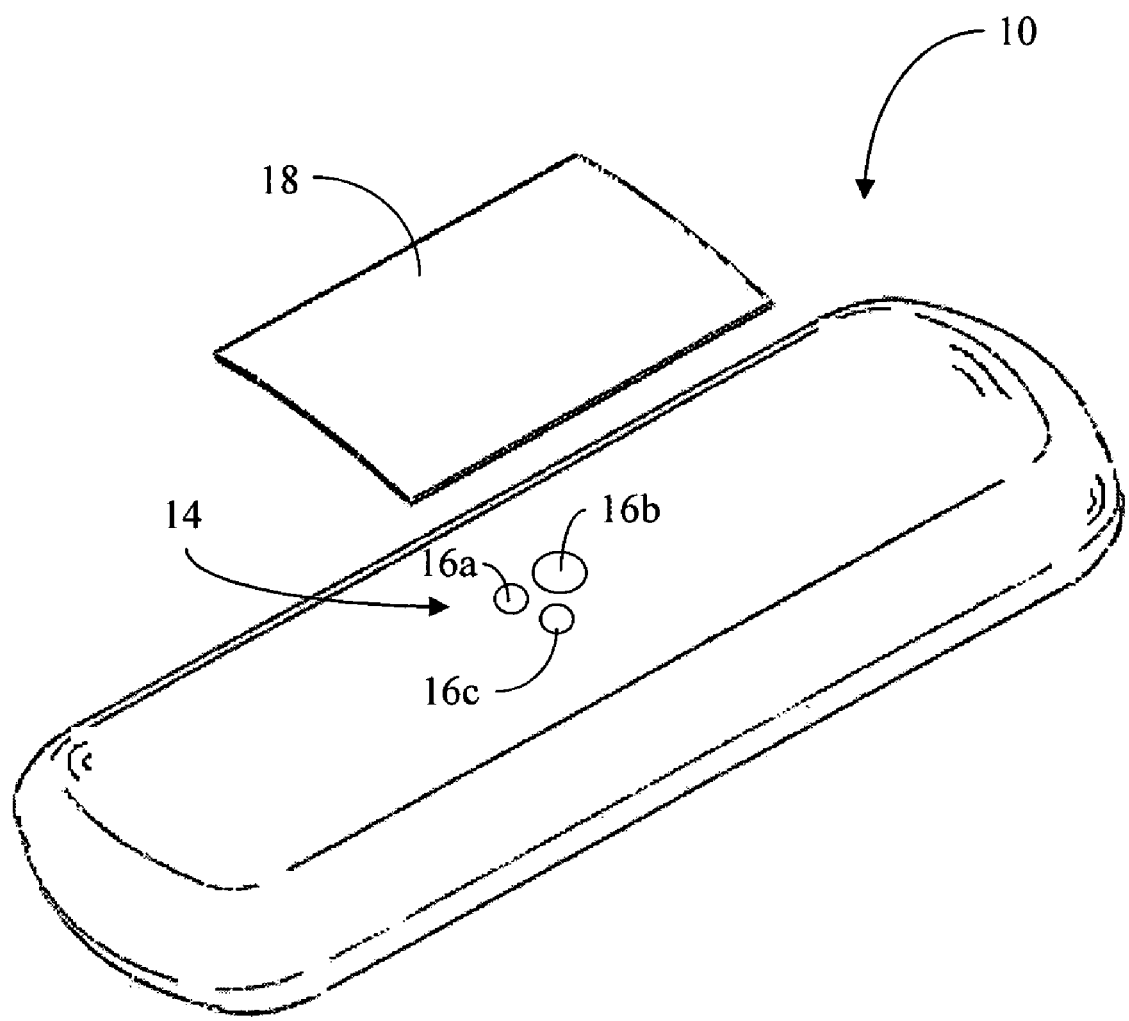
FIG. 1 is an exploded perspective view of one exemplary embodiment of a implantable glucose sensor.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The term "signal output," as used herein, is a broad term and is used in its ordinary sense, including, without limitation, an analog or digital signal directly related to the measured analyte from the analyte-measuring device. The term broadly encompasses a single point, or alternatively, a plurality of time spaced data points from a substantially continuous glucose sensor, which comprises individual measurements taken at time intervals ranging from fractions of a second up to, for example, 1, 2, or 5 minutes or longer.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "potentiostat," as used herein, is a broad term and is used in its ordinary sense, including, without limitation, an electrical system that controls the potential between the working and reference electrodes of a three-electrode cell at a preset value independent of resistance changes between the electrodes. It forces whatever current is necessary to flow between the working and counter electrodes to keep the desired potential, as long as the cell voltage and current do not exceed the compliance limits of the potentiostat.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. The sensing region generally comprises a non-conductive body, a working electrode, a reference electrode, and optionally a counter electrode passing through and secured within the body forming electrochemically reactive surfaces on the body and an electronic connective means at another location on the body, and a multi-domain membrane system affixed to the body and covering the electrochemically reactive surface.

The terms "raw data stream" and "data stream," as used herein, are broad terms and are used in their ordinary sense, including, without limitation, an analog or digital signal directly related to the measured an analyte from an analyte sensor. In one example, the raw data stream is digital data in "counts" converted by an A/D converter from an analog signal (for example, voltage or amps) representative of a analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The terms "electrical potential" and "potential" as used herein, are broad terms and are used in their ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, a sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts that have a higher amplitude than system noise," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and characterized by a higher amplitude than system noise.

The term "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview

The preferred embodiments relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples.

The sensor uses any known method, including invasive, minimally invasive, and non-invasive sensing techniques, to provide an output signal indicative of the concentration of the analyte of interest. The sensor is of the type that senses a product or reactant of an enzymatic reaction between an analyte and an enzyme in the presence of oxygen as a measure of the analyte in vivo or in vitro. Such a sensor typically comprises a membrane surrounding the enzyme through which a bodily fluid passes and in which an analyte within the bodily fluid reacts with an enzyme in the presence of oxygen to generate a product. The product is then measured using electrochemical methods and thus the output of an electrode system functions as a measure of the analyte. In some embodiments, the sensor can use an amperometric, coulometric, conductimetric, and/or potentiometric technique for measuring the analyte. In some embodiments, the electrode system can be used with any of a variety of known in vitro or in vivo analyte sensors or monitors.

FIG. 1 is an exploded perspective view of one exemplary embodiment of an implantable glucose sensor 10 that utilizes an electrode system 16. In this exemplary embodiment, a body with a sensing region 14 includes an electrode system (16a to 16c), also referred to as the electroactive sensing surface, and sensor electronics, which are described in more detail with reference to FIG. 2.

In this embodiment, the electrode system 16 is operably connected to the sensor electronics (FIG. 2) and includes electroactive surfaces (including two-, three- or more electrode systems), which are covered by a membrane system 18. The membrane system 18 is disposed over the electroactive surfaces of the electrode system 16 and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, such as described in co-pending U.S. patent application Ser. No. 10/838,912, filed May 3, 2004 and entitled "IMPLANTABLE ANALYTE SENSOR," the contents of which are incorporated herein by reference in their entirety. The membrane system can be attached to the sensor body by mechanical or chemical methods such as described in co-pending U.S. patent application Ser. No. 10/885,476, filed Jul. 6, 2004 and entitled, "SYSTEMS AND METHODS FOR MANUFACTURE OF AN ANALYTE-MEASURING DEVICE INCLUDING A MEMBRANE SYSTEM" and U.S. patent application Ser. No. 10/838,912 filed May 3, 2004 and entitled, "IMPLANTABLE ANALYTE SENSOR", which are incorporated herein by reference in their entirety.

In the embodiment of FIG. 1, the electrode system 16 includes three electrodes (working electrode 16a, counter electrode 16b, and reference electrode 16c), wherein the counter electrode is provided to balance the current generated by the species being measured at the working electrode. In the case of a glucose oxidase based glucose sensor, the species measured at the working electrode is $H_2O_2$. Glucose oxidase, GOX, catalyzes the conversion of oxygen and glucose to hydrogen peroxide and gluconate according to the following reaction:

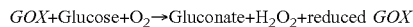

$$GOX + Glucose + O_2 \rightarrow Gluconate + H_2O_2 + \text{reduced } GOX$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H+), two electrons (2e−), and one oxygen molecule ($O_2$). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In some embodiments, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, one limitation of prior art enzymatic-based electrochemical analyte sensors can be caused by oxygen deficiencies, which is described in more detail with reference to FIG. 3.

Figure 2:
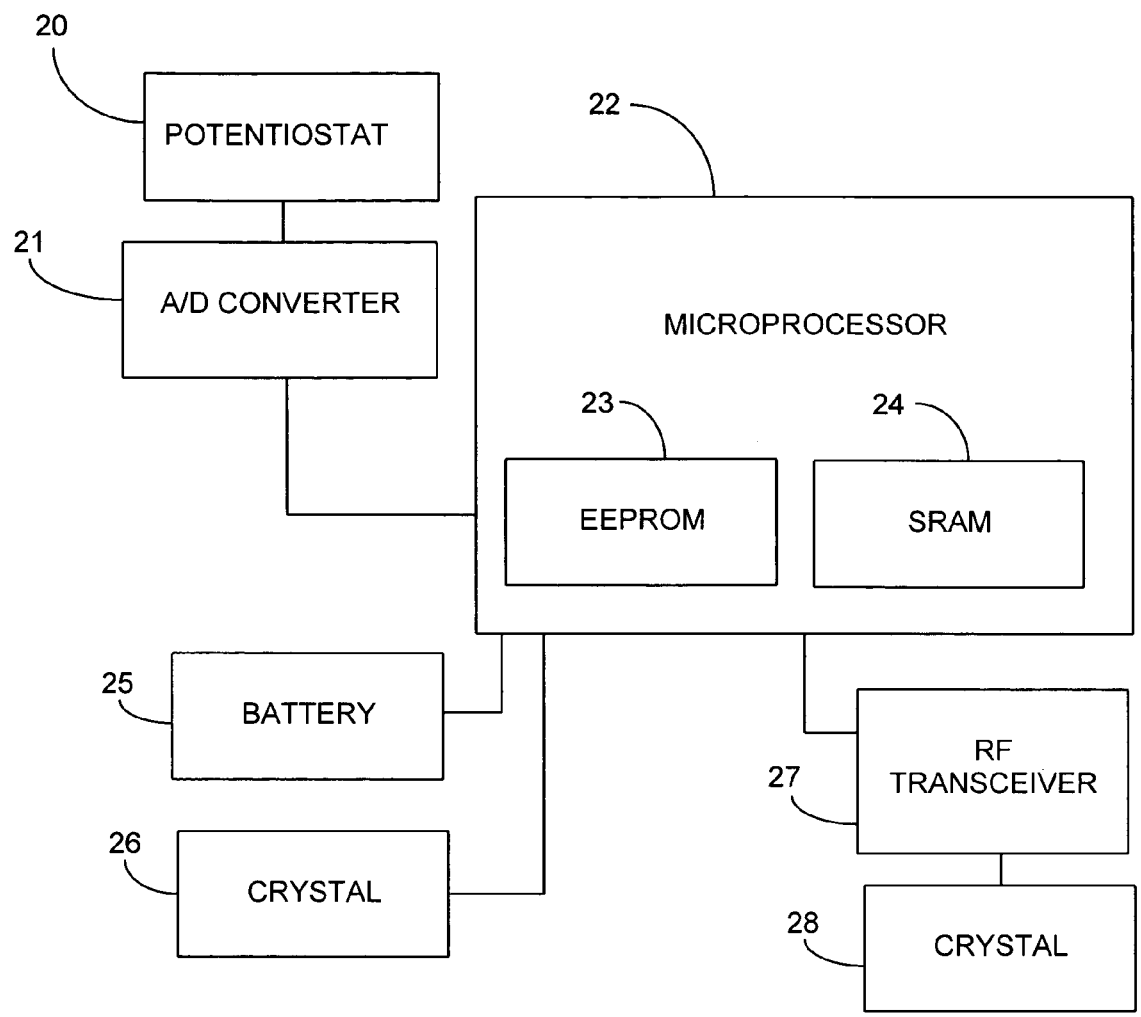
FIG. 2 is a block diagram that illustrates sensor electronics in one exemplary embodiment.

FIG. 2 is a block diagram that illustrates sensor electronics in one exemplary embodiment; one skilled in the art appreciates however that a variety of sensor electronics configurations can be implemented with the preferred embodiments. In this embodiment, a potentiostat 20 is shown, which is operatively connected to electrode system 16 (FIG. 1) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and necessary programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the necessary power for the sensor. In one embodiment, the battery is a Lithium Manganese Dioxide battery, however any appropriately sized and powered battery can be used. In some embodiments, a plurality of batteries can be used to power the system. Quartz crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Although FIGS. 1 and 2 and associated text illustrate and describe an exemplary embodiment of an implantable glucose sensor, the electrode systems of the preferred embodiments described below can be implemented with any known electrochemical sensor, including U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al; to U.S. Pat. No. 5,985,129 to Gough et al.; WO Patent Application Publication No. 2004/021877 to Caduff; U.S. Pat. No. 5,494,562 to Maley et al.; U.S. Pat. No. 6,120,676 to Heller et al.; and U.S. Pat. No. 6,542,765 to Guy et al., co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA," the contents of each of which are incorporated herein by reference in their entirety.

Figure 3:
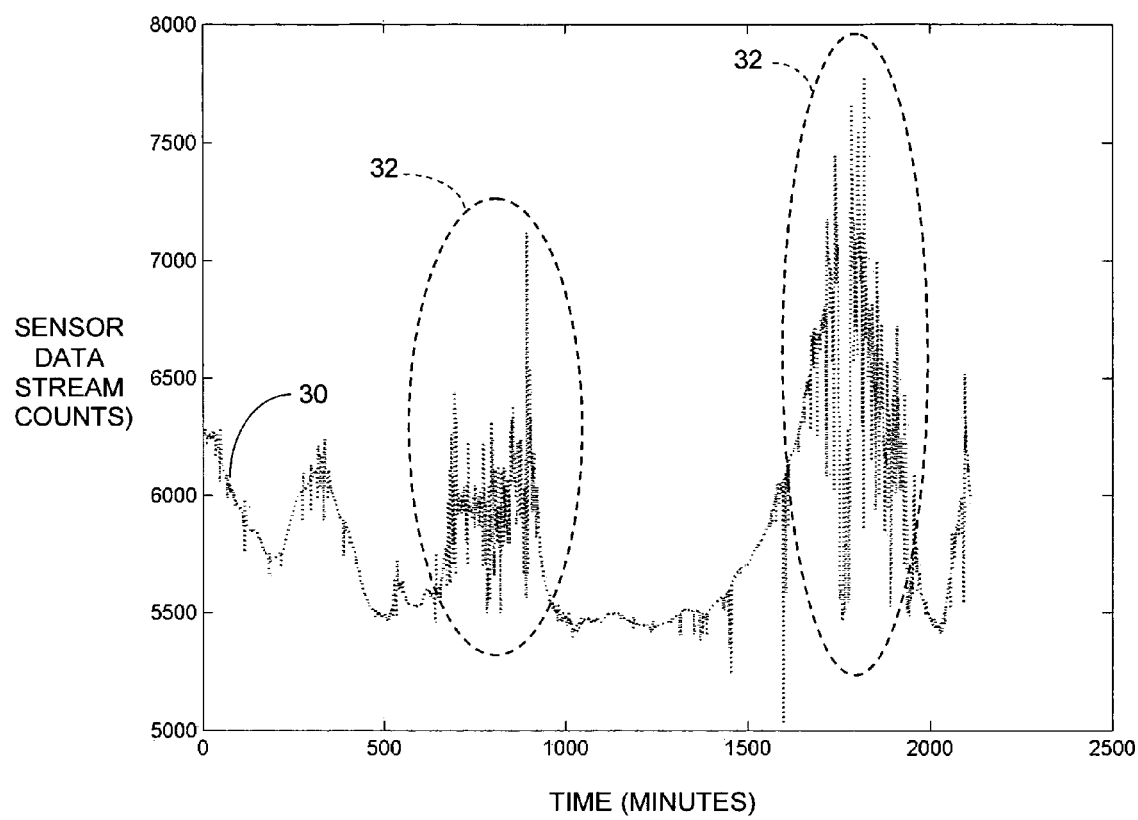
FIG. 3 is a graph that shows a raw data stream obtained from a glucose sensor without an auxiliary electrode of the preferred embodiments.

FIG. 3 is a graph that depicts a raw data stream obtained from a prior art glucose sensor such as described with reference to FIG. 1. The x-axis represents time in minutes. The y-axis represents sensor data in counts. In this example, sensor output in counts is transmitted every 30-seconds. The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

In one situation, when oxygen is deficient relative to the amount of glucose, then the enzymatic reaction is limited by oxygen rather than glucose. Thus, the output signal is indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which could be ground or 0.0 V, which causes the reference to shift, reducing the bias voltage, such is as described in more detail below. In other words, a common result of ischemia a drop off in sensor current as a function of glucose concentration (for example, lower sensitivity). This happens because the working electrode no longer oxidizes all of the $H_2O_2$ arriving at its surface because of the reduced bias. In some extreme circumstances, an increase in glucose can produce no increase in current or even a decrease in current.

In some situations, transient ischemia can occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries resulting in local ischemia and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), cholesterol (cholesterol oxidase), or the like.

Another problem with conventional electrochemical sensors is that they can electrochemically react not only with the analyte to be measured (or by-product of the enzymatic reaction with the analyte), but additionally can react with other electroactive species that are not intentionally being measured (for example, interfering species), which causes an increase in signal strength due to these "interfering species". In other words, interfering species are compounds with an oxidation or reduction potential that overlaps with the analyte to be measured (or the by-product of the enzymatic reaction with the analyte). For example, in a conventional amperometric glucose oxidase-based glucose sensor wherein the sensor measures hydrogen peroxide, interfering species such as acetaminophen, ascorbate, and urate are known to produce inaccurate signal strength when they are not properly controlled.

Some conventional glucose sensors utilize a membrane system that blocks at least some interfering species, such as ascorbate and urate. In some such systems, at least one layer of the membrane system includes a porous structure that has a relatively impermeable matrix with a plurality of "micro holes" or pores of molecular dimensions, such that transfer through these materials is primarily due to passage of species through the pores (for example, the layer acts as a microporous barrier or sieve blocking interfering species of a particular size). In other such systems, at least one layer of the membrane system defines a permeability that allows selective dissolution and diffusion of species as solutes through the layer. Unfortunately, it is difficult to find membranes that are satisfactory or reliable in use, especially in vivo, which effectively block all interferants and/or interfering species in some embodiments.

Electrochemical Sensors of the Preferred Embodiments

In one aspect of the preferred embodiments, an electrochemical sensor is provided with an auxiliary electrode configured to generate oxygen in order to overcome the effects of transient ischemia. In another aspect of the preferred embodiments, an electrochemical sensor is provided with an auxiliary electrode configured to electrochemically modify (for example, oxidize or reduce) electrochemical interferants to render them substantially non-electroactively reactive at the electroactive sensing surface(s) in order to overcome the effects of interferants on the working electrode.

It is known that oxygen can be generated as a product of electrochemical reactions occurring at a positively charged electrode (for example, set at about +0.6 to about +1.2 V or more). One example of an oxygen producing reaction is the electrolysis of water, which creates oxygen at the anode (for example, the working electrode). In the exemplary electrochemical glucose sensor, glucose is converted to hydrogen peroxide by reacting with glucose oxidase and oxygen, after which the hydrogen peroxide is oxidized at the working electrode and oxygen is generated therefrom. It is noted that one challenge to generating oxygen electrochemically in this way is that while an auxiliary electrode does produce excess oxygen, the placement of the auxiliary electrode in proximity to the analyte-measuring working electrode can cause oxidation of hydrogen peroxide at the auxiliary electrode, resulting in reduced signals at the working electrode. It is also known that many electrochemical interferants can be reduced at a potential of from about +0.1V to +1.2V or more; for example, acetaminophen is reduced at a potential of about +0.4 V.

Accordingly, the sensors of preferred embodiments place an auxiliary electrode above the electrode system 16, or other electroactive sensing surface, thereby reducing or eliminating the problem of inaccurate signals as described above.

Figure 4:
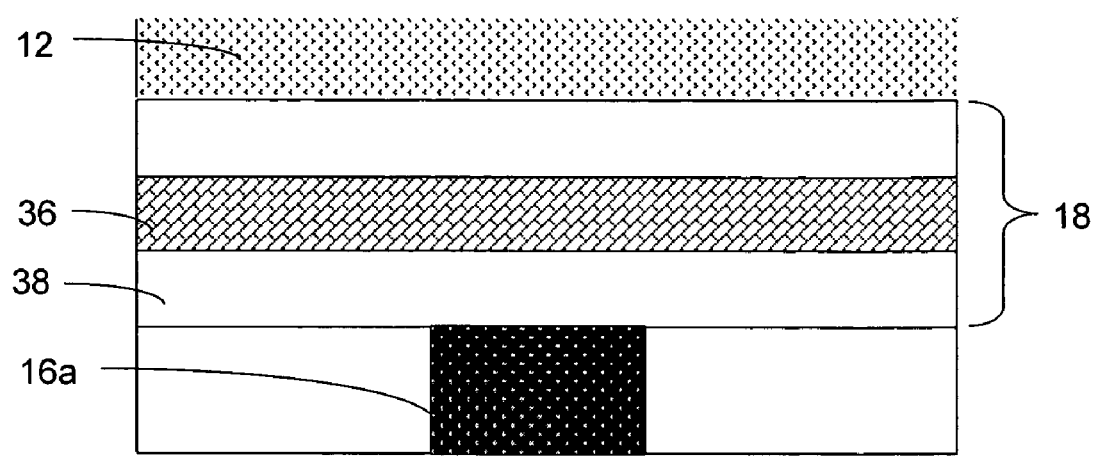
FIG. 4 is a side schematic illustration of a portion of an electrochemical sensor of the preferred embodiments, showing an auxiliary electrode placed proximal to the enzyme domain within a membrane system.

FIG. 4 is a side schematic illustration of a portion of the sensing region of an electrochemical sensor of the preferred embodiments, showing an auxiliary electrode between the enzyme and the outside solution while the working (sensing) electrode is located below the enzyme and further from the outside solution. Particularly, FIG. 4 shows an external solution 12, which represents the bodily or other fluid to which the sensor is exposed in vivo or in vitro.

The membrane system 18 includes a plurality of domains (for example, cell impermeable domain, resistance domain, enzyme domain, and/or other domains such as are described in U.S. Published Patent Application 2003/0032874 to Rhodes et al. and copending U.S. patent application Ser. No. 10/885,476, filed Jul. 6, 2004 and entitled, "SYSTEMS AND METHODS FOR MANUFACTURE OF AN ANALYTE-MEASURING DEVICE INCLUDING A MEMBRANE SYSTEM", the contents of which are incorporated herein by reference in their entireties) is located proximal to the external solution and finctions to transport fluids necessary for the enzymatic reaction, while protecting inner components of the sensor from harsh biohazards, for example. Although each domain is not independently shown, the enzyme 38 is shown disposed between an auxiliary electrode 36 and the working electrode 16a in the illustrated embodiment.

Preferably, the auxiliary electrode 36 is located within or adjacent to the membrane system 18, for example, between the enzyme and other domains, although the auxiliary electrode can be placed anywhere between the electroactive sensing surface and the outside fluid. The auxiliary electrode 36 is formed from known working electrode materials (for example, platinum, palladium, graphite, gold, carbon, conductive polymer, or the like) and has a voltage setting that produces oxygen (for example, from about +0.6 V to +1.2 V or more) and/or that electrochemically modifies (for example, reduces) electrochemical interferants to render them substantially non-reactive at the electroactive sensing surface(s) (for example, from about +0.1 V to +1.2 V or more). The auxiliary electrode can be a mesh, grid, plurality of spaced wires or conductive polymers, or other configurations designed to allow analytes to penetrate therethrough.

In the aspect of the preferred embodiments wherein the auxiliary electrode 36 is configured to generate oxygen, the oxygen generated from the auxiliary electrode 36 diffuses upward and/or downward to be utilized by the enzyme 38 and/or the counter electrode (depending on the placement of the auxiliary electrode). Additionally, the analyte (for example, glucose) from the outside solution (diffuses through the auxiliary electrode 36) reacts with the enzyme 38 and produces a measurable product (for example, hydrogen peroxide). Therefore, the product of the enzymatic reaction diffuses down to the working electrode 16a for accurate measurement without being eliminated by the auxiliary electrode 36.

In one alternative embodiment, the auxiliary electrode 36 can be coated with a polymeric material, which is impermeable to glucose but permeable to oxygen. By this coating, glucose will not electroactively react at the auxiliary electrode 36, which can otherwise cause at least some of the glucose to pre-oxidize as it passes through the auxiliary electrode 36 (when placed above the enzyme), which can prevent accurate glucose concentration measurements at the working electrode in some sensor configurations. In one embodiment, the polymer coating comprises silicone, however any polymer that is selectively permeable to oxygen, but not glucose, can be used. The auxiliary electrode 16 can be coated by any known process, such as dip coating or spray coating, after which is can be blown, blotted, or the like to maintain spaces within the electrode for glucose transport.

In another alternative embodiment, the auxiliary electrode 36 can be coated with a polymeric material that is permeable to glucose and oxygen and can be placed between the enzyme and the outside fluid. Consequently, the polymeric coating will cause glucose from the outside fluid to electroactively react at the auxiliary electrode 36, thereby limiting the amount of glucose that passes into the enzyme 38, and thus reducing the amount of oxygen necessary to successfully react with all available glucose in the enzyme. The polymeric material can function in place of or in combination with the resistance domain in order to limit the amount of glucose that passes through the membrane system. This embodiment assumes a stoichiometric relationship between glucose oxidation and decreased sensor signal output, which can be compensated for by calibration in some sensor configurations. Additionally, the auxiliary electrode generates oxygen, further reducing the likelihood of oxygen becoming a rate-limiting factor in the enzymatic reaction and/or at the counter electrode, for example.

In another aspect of the preferred embodiments, the auxiliary electrode 36 is configured to electrochemically modify (for example, oxidize or reduce) electrochemical interferants to render them substantially non-reactive at the electroactive sensing surface(s). In these embodiments, which can be in addition to or alternative to the above-described oxygen-generating embodiments, a polymer coating is chosen to selectively allow interferants (for example, urate, ascorbate, and/or acetaminophen such as described in U.S. Pat. No. 6,579,690 to Bonnecaze, et al.) to pass through the coating and electrochemically react with the auxiliary electrode, which effectively pre-oxidizes the interferants, rendering them substantially non-reactive at the working electrode 16a. In one exemplary embodiment, silicone materials can be synthesized to allow the transport of oxygen, acetaminophen and other interferants, but not allow the transport of glucose. In some embodiments, the polymer coating material can be chosen with a molecular weight that blocks glucose and allows the transport of oxygen, urate, ascorbate, and acetaminophen. In another exemplary embodiment, silicone materials can be synthesized to allow the transport of oxygen, glucose, acetaminophen, and other interferants. In some embodiments, the polymer coating material is chosen with a molecular weight that allows the transport of oxygen, glucose, urate, ascorbate, and acetaminophen. The voltage setting necessary to react with interfering species depends on the target electrochemical interferants, for example, from about +0.1 V to about +1.2 V. In some embodiments, wherein the auxiliary electrode is set at a potential of from about +0.6 to about +1.2 V, both oxygen-generation and electrochemical interferant modification can be achieved. In some embodiments, wherein the auxiliary electrode is set at a potential below about +0.6 V, the auxiliary electrode will function mainly to electrochemically modify interferants, for example.

Therefore, the sensors of preferred embodiments reduce or eliminate oxygen deficiency problems within electrochemical sensors by producing oxygen at an auxiliary electrode located above the enzyme within an enzyme-based electrochemical sensor. Additionally or alternatively, the sensors of preferred embodiments reduce or eliminate interfering species problems by electrochemically reacting with interferants at the auxiliary electrode rendering them substantially non-reactive at the working electrode.

Methods and devices that are suitable for use in conjunction with aspects of the preferred embodiments are disclosed in co-pending U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. application Ser. No. 60/489,615 filed Jul. 23, 2003 and entitled "ROLLED ELECTRODE ARRAY AND ITS METHOD FOR MANUFACTURE"; U.S. application Ser. No. 60/490,010 filed Jul. 25, 2003 and entitled "INCREASING BIAS FOR OXYGEN PRODUCTION IN AN ELECTRODE ASSEMBLY"; U.S. application Ser. No. 60/490,009 filed Jul. 25, 2003 and entitled "OXYGEN ENHANCING ENZYME MEMBRANE FOR ELECTROCHEMICAL SENSORS"; U.S. application Ser. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed Jul. 21, 2004 and entitled "ROLLED ELECTRODE ARRAY AND ITS METHOD FOR MANUFACTURE"; U.S. application Ser. No. 10/896,772 filed Jul. 21, 2004 and entitled "INCREASING BIAS FOR OXYGEN PRODUCTION IN AN ELECTRODE SYSTEM"; U.S. application Ser. No. 10/896,639 filed Jul. 21, 2004 and entitled "OXYGEN ENHANCING MEMBRANE SYSTEMS FOR IMPLANTABLE DEVICES"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical sensor for determining a presence or a concentration of an analyte in a fluid, the sensor comprising:
   a membrane system comprising an enzyme, wherein the enzyme reacts with the analyte;
   an electroactive surface comprising a working electrode, the working electrode comprising a conductive material and configured to measure a product of the reaction of the enzyme with the analyte; and
   an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is situated on a surface of the auxiliary electrode, and wherein the polymer comprises a material that is directly impermeable to glucose but is permeable to oxygen.

2. The electrochemical sensor of claim 1, wherein the auxiliary electrode comprises a conductive material selected from the group consisting of a conductive metal, a conductive polymer, and a blend of a conductive metal and a conductive polymer.

3. The electrochemical sensor of claim 1, wherein the auxiliary electrode comprises a form selected from the group consisting of a mesh, a grid, and a plurality of spaced wires.

4. The electrochemical sensor of claim 1, wherein the polymer comprises a material that is permeable to interfering species.

5. The electrochemical sensor of claim 4, wherein the polymer comprises a material having a molecular weight that allows transport therethrough of oxygen, urate, ascorbate, and acetaminophen.

6. The electrochemical sensor of claim 1, wherein the auxiliary electrode is configured to be set at a potential of at least about +0.6 V.

7. The electrochemical sensor of claim 1, wherein the auxiliary electrode is configured to electrochemically modify an electrochemical interferant to render the electrochemical interferent substantially electrochemically non-reactive at the working electrode.

8. The electrochemical sensor of claim 7, wherein the auxiliary electrode is configured to be set at a potential of at least about +0.1 V.

9. The electrochemical sensor of claim 1, configured for measuring a concentration of glucose in a fluid.

10. The electrochemical sensor of claim 1, configured for insertion into a subcutaneous tissue of a host.

11. The electrochemical sensor of claim 1, configured for implantation into a subcutaneous tissue of a host.

12. The electrochemical sensor of claim 1, configured for measuring a concentration of glucose substantially without an oxygen deficit.

13. An electrochemical sensor for determining a presence or a concentration of an analyte in a fluid, the sensor comprising:
   a membrane system comprising an enzyme, wherein the enzyme reacts with the analyte;
   an electroactive surface comprising a working electrode, the working electrode comprising a conductive material and configured to measure a product of the reaction of the enzyme with the analyte; and
   an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is directly situated on a surface of the auxiliary electrode, and wherein the polymer comprises a material that is impermeable to glucose but is permeable to oxygen and permeable to interfering species.

14. The electrochemical sensor of claim 13, wherein the polymer comprises a material having a molecular weight that blocks glucose and allows transport therethrough of oxygen, urate, ascorbate, and acetaminophen.

15. The electrochemical sensor of claim 13, wherein the auxiliary electrode comprises a conductive material selected from the group consisting of a conductive metal, a conductive polymer, and a blend of a conductive metal and a conductive polymer.

16. The electrochemical sensor of claim 13, wherein the auxiliary electrode comprises a form selected from the group consisting of a mesh, a grid, and a plurality of spaced wires.

17. The electrochemical sensor of claim 13, wherein the polymer comprises a material having a molecular weight that allows transport therethrough of urate, ascorbate, and acetaminophen.

18. The electrochemical sensor of claim 13, wherein the auxiliary electrode is configured to be set at a potential of at least about +0.6 V.

19. The electrochemical sensor of claim 13, wherein the auxiliary electrode is configured to electrochemically modify an electrochemical interferant to render the electrochemical interferent substantially electrochemically non-reactive at the working electrode.

20. The electrochemical sensor of claim 19, wherein the auxiliary electrode is configured to be set at a potential of at least about +0.1 V.

21. The electrochemical sensor of claim 13, configured for measuring a concentration of glucose in a fluid.

22. The electrochemical sensor of claim 13, configured for insertion into a subcutaneous tissue of a host.

23. The electrochemical sensor of claim 13, configured for implantation into a subcutaneous tissue of a host.

24. The electrochemical sensor of claim 13, configured for measuring a concentration of glucose substantially without an oxygen deficit.

25. An electrochemical sensor for determining a presence or a concentration of an analyte in a fluid, the sensor comprising:
   a membrane system comprising an enzyme, wherein the enzyme reacts with the analyte;
   an electroactive surface comprising a working electrode, the working electrode comprising a conductive material and configured to measure a product of the reaction of the enzyme with the analyte; and
   an auxiliary electrode comprising a conductive material and configured to modify an electrochemical interferant such that the electrochemical interferent is rendered substantially electrochemically non-reactive at the working electrode, wherein the auxiliary electrode comprises a polymer, wherein the polymer is situated on a surface of the auxiliary electrode, and wherein the polymer comprises a material that is impermeable to glucose but is permeable to oxygen.

26. The electrochemical sensor of claim 25, wherein the auxiliary electrode comprises a conductive material selected from the group consisting of a conductive metal, a conductive polymer, and a blend of a conductive metal and a conductive polymer.

27. The electrochemical sensor of claim 25, wherein the auxiliary electrode comprises a form selected from the group consisting of a mesh, a grid, and a plurality of spaced wires.

28. The electrochemical sensor of claim 25, wherein the polymer comprises a material that is permeable to an electrochemical interferant.

29. The electrochemical sensor of claim 25, wherein the polymer comprises a material that is impermeable to glucose but is permeable to oxygen and interferants.

30. The electrochemical sensor of claim 25, wherein the auxiliary electrode is configured to be set at a potential of at least about +0.1V.

31. The electrochemical sensor of claim 25, wherein the auxiliary electrode is configured to generate oxygen.

32. The electrochemical sensor of claim 31, wherein the auxiliary electrode is configured to be set at a potential of at least about +0.6 V.

33. The electrochemical sensor of claim 25, configured for measuring a concentration of glucose in a fluid.

34. The electrochemical sensor of claim 25, configured for insertion into a subcutaneous tissue of a host.

35. The electrochemical sensor of claim 25, configured for implantation into a subcutaneous tissue of a host.

36. The electrochemical sensor of claim 25, configured for measuring a concentration of glucose substantially without an oxygen deficit.

37. The electrochemical sensor of claim 25, wherein the auxiliary electrode is configured to generate oxygen.

38. The electrochemical sensor of claim 37, wherein the auxiliary electrode is configured to be set at a potential of at least about +0.6 V.

39. An electrochemical sensor for determining a presence or a concentration of an analyte in a fluid, the sensor comprising:
    a membrane system comprising an enzyme, wherein the enzyme reacts with the analyte;
    an electroactive surface comprising a working electrode, the working electrode comprising a conductive material and configured to measure a product of the reaction of the enzyme with the analyte; and
    an auxiliary electrode comprising a conductive material and configured to modify an electrochemical interferant such that the electrochemical interferant is rendered substantially electrochemically non-reactive at the working electrode, wherein the auxiliary electrode comprises a polymer, wherein the polymer is situated on a surface of the auxiliary electrode, and wherein the polymer comprises a material having a molecular weight that blocks glucose and allows transport therethrough of oxygen, urate, ascorbate, and acetaminophen.

40. The electrochemical sensor of claim 39, wherein the auxiliary electrode comprises a conductive material selected from the group consisting of a conductive metal, a conductive polymer, and a blend of a conductive metal and a conductive polymer.

41. The electrochemical sensor of claim 39, wherein the auxiliary electrode comprises a form selected from the group consisting of a mesh, a grid, and a plurality of spaced wires.

42. The electrochemical sensor of claim 39, wherein the polymer comprises a material that is permeable to an electrochemical interferant.

43. The electrochemical sensor of claim 39, wherein the polymer comprises a material that is permeable to interferants.

44. The electrochemical sensor of claim 39, wherein the auxiliary electrode is configured to be set at a potential of at least about +0.1V.

45. The electrochemical sensor of claim 39, wherein the auxiliary electrode is configured to generate oxygen.

46. The electrochemical sensor of claim 45, wherein the auxiliary electrode is configured to be set at a potential of at least about +0.6 V.

47. The electrochemical sensor of claim 39, configured for measuring a concentration of glucose in a fluid.

48. The electrochemical sensor of claim 39, configured for insertion into a subcutaneous tissue of a host.

49. The electrochemical sensor of claim 39, configured for implantation into a subcutaneous tissue of a host.

50. The electrochemical sensor of claim 39, configured for measuring a concentration of glucose substantially without an oxygen deficit.

* * * * *